(12) United States Patent
Lu

(10) Patent No.: US 10,456,367 B2
(45) Date of Patent: *Oct. 29, 2019

(54) COMPOSITIONS AND METHODS FOR TREATING MUSCULAR DYSTROPHY AND OTHER DISORDERS

(71) Applicant: The Charlotte Mecklenburg Hospital Authority, Charlotte, NC (US)

(72) Inventor: Qi Long Lu, Charlotte, NC (US)

(73) Assignee: The Charlotte Mecklenburg Hospital Authority, Charlotte, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/151,126

(22) Filed: Oct. 3, 2018

(65) Prior Publication Data

US 2019/0054037 A1 Feb. 21, 2019

Related U.S. Application Data

(62) Division of application No. 15/842,580, filed on Dec. 14, 2017, now Pat. No. 10,245,235.

(60) Provisional application No. 62/520,252, filed on Jun. 15, 2017, provisional application No. 62/435,442, filed on Dec. 16, 2016.

(51) Int. Cl.
*A61K 31/47* (2006.01)
*A61K 31/047* (2006.01)
*A61P 21/00* (2006.01)
*A61K 31/7004* (2006.01)

(52) U.S. Cl.
CPC ........ *A61K 31/047* (2013.01); *A61K 31/7004* (2013.01); *A61P 21/00* (2018.01)

(58) Field of Classification Search
None
See application file for complete search history.

(56) References Cited

U.S. PATENT DOCUMENTS

| 2010/0197612 A1 | 8/2010 | Ko |
| 2010/0209388 A1 | 8/2010 | Mazzio et al. |
| 2011/0008418 A1 | 1/2011 | Ko |

OTHER PUBLICATIONS

Chan et al. (Human Molecular Genetics 19:3995-4006, 2010) (Year: 2010).*
Awano et al. (Am J Pathol 185:2025-2037, 2015) (Year: 2015).*
Gerin et al. (Nature Communications 7:11534, pp. 1-15 (published May 19, 2016) (Year: 2016).*
Awano et al. "Dystroglycanopathy muscles lacking functional glycosylation of alpha-dystroglycan retain regeneration capacity" Neuromuscular Disorders, 25(6):474-484 (2015) (Abstract only).

Awano et al. "Restoration of Functional Glycosylation of alpha-Dystroglycan in FKRP Mutant Mice Is Associated with Muscle Regeneration" The American Journal of Pathology, 185(7):2025-2037 (2015) (Abstract only).
Beltran-Valero et al. "Binding in Epithelium-derived Cancers is Caused by Silencing of LARGE" The Journal of Biological Chemistry, 284(17):11279-11284 (2009).
Beltran-Valero et al. "Mutations in the FKRP gene can cause muscle-eye-brain disease and Walker-Warburg syndrome" J. Med. Genet., 41: e61 (2004).
Benitez-Guerrero et al. "A role for dystroglycan in the pathophysiology of acute leukemic cells" Life Sciences, 182:1-9 (2017).
Blaeser et al. "Distinct expression of functionally glycosylated alpha-dystroglycan in muscle and non-muscle tissues of FKRP mutant mice" PLoS ONE, 13(1):e0191016 (17 pages) (2018).
Blaeser et al. "Mouse models of fukutin-related protein mutations show a wide range of disease phenotypes" Human Genetics, 132:923-934 (2013).
Blaeser et al. "Progressive Dystrophic Pathology in Diaphragm and Impairment of Cardiac Function in FKRP P448L Mutant Mice" PLoS ONE, 11(10): e0164187 (16 pages) (2016).
Bourteel et al. "Clinical and mutational spectrum of limb-girdle muscular dystrophy type 2I in 11 French patients" J. Neurol. Neurosurg. Psychiatry, 80:1405-1408 (2009) (Abstract only).
Briggs et al. "Structural basis of laminin binding to the LARGE glycans on dystroglycan" Nat. Chem. Biol., 12:810-814 (2016).
Brockington et al. "Mutations in the fukutin-related protein gene (FKRP) cause a form of congenital muscular dystrophy with secondary laminin alpha2 deficiency and abnormal glycosylation of alpha-dystoglycan" Am. J. Hum. Genet., 69:1198-1209 (2001) (Abstract only).
Brockington et al. "Mutations in the fukutin-related protein gene (FKRP) identify limb girdle muscular dystrophy 2I as a milder allelic variant of congenital muscular dystrophy MDC1C" Human Molecular Genetics, 10(25):2851-2859 (2001).
Brown et al. "220th ENMC workshop: Dystroglycan and the dystroglycanopathies Naarden the Netherlands, May 27-29, 2016" Neuromuscular Disord. NMD, 27:387-395 (2017).
Brown et al. "Abnormalities in alpha-dystroglycan expression in MDC1C and LGMD2I muscular dystrophies" Am. J. Pathol., 164:727-737 (2004).
Chan et al. "Fukutin-related protein is essential for mouse muscle, brain and eye development and mutation recapitulates the wide clinical spectrums of dystroglycanopathies" Human Molecular Genetics, 19(20):3995-4006 (2010).
Cohn et al. "Disruption of DAG1 in differentiated skeletal muscle reveals a role for dystroglycan in muscle regeneration" Cell, 110(5):639-648 (2002) (Abstract only).
Endo, T. "Dystroglycan glycosylation and its role in alpha-dystroglycanopathies" Acta Myologica, 26(3):165-170 (2007).
Ervasti et al. "A role for the dystrophin-glycoprotein complex as a transmembrane linker between laminin and actin" J. Cell. Biol., 122:809-823 (1993).
Ervasti et al. "Membrane organization of the dystrophin-glycoprotein complex" Cell, 66:1121-1131 (1991) (Abstract only).
Esapa et al. "Functional requirements for fukutin-related protein in the Golgi apparatus" Hum. Mol. Genet., 11:3319-3331 (2002) ) (Abstract only).

(Continued)

*Primary Examiner* — Craig D Ricci
(74) *Attorney, Agent, or Firm* — Myers Bigel, P.A.

(57) ABSTRACT

The present invention provides compositions and methods of their use in treating muscular dystrophy and other disorders.

2 Claims, 11 Drawing Sheets

(56) References Cited

OTHER PUBLICATIONS

Frattini et al. "Autologous intramuscular transplantation of engineered satellite cells induces exosome-mediated systemic expression of Fukutin-related protein and rescues disease phenotype in a murine model of limb-girdle muscular dystrophy type 2I" Human Molecular Genetics, 26(19):3682-3698 (2017).
Frosk et al. "The most common mutation in FKRP causing limb girdle muscular dystrophy type 2I (LGMD2I) may have occurred only once and is present in Hutterites and other populations" Hum. Mutat., 25:38-44 (2005) (Abstract only).
Gee et al. "Dystroglycan-alpha, a dystrophin-associated glycoprotein, is a functional agrin receptor" Cell, 77:675-686 (1994) (Abstract only).
Gerin et al. "ISPD produces CDP-ribitol used by FKTN and FKRP to transfer ribitol phosphate onto alpha-dystroglycan" Nature Communications, 7(11534):1-15 (2016).
Gicquel et al. "AAV-mediated transfer of FKRP shows therapeutic efficacy in a murine model but requires control of gene expression" Human Molecular Genetics, 26(10):1952-1965 (2017).
Godfrey et al. "Dystroglycanopathies: coming into focus" Current Opinion in Genetics & Development, 21(3):278-285 (2011) (Abstract only).
Hewitt, Jane E. "Abnormal glycosylation of dystroglycan in human genetic disease" Biochimica et Biophysica Acta, 1792:853-861 (2009).
Hillier "Diamonds are forever: the cortisone legacy" J. Endocrinol., 195:1-6 (2007) (Abstract only).
Hiruma et al. "A novel human beta1,3-N-acetylgalactosaminyltransferase that synthesizes a unique carbohydrate structure GaINAcbeta1-3GlcNAc" J. Biol. Chem., 279:14087-14095 (2004) (Abstract only).
Inamori et al. "Dystroglycan function requires xylosyl- and glucuronyltransferase activities of LARGE" Science, 335:93-96 (2012).
Jimenez-Mallebrera et al. "A comparative study of alpha-dystroglycan glycosylation in dystroglycanopathies suggests that the hypoglycosylation of alpha-dystroglycan does not consistently correlate with clinical severity" Brain Pathol., 19(4):596-611(2009).
Kanagawa et al. "Identification of a Post-translational Modification with Ribitol-Phosphate and Its Defect in Muscular Dystrophy" Cell Reports, 14:2209-2223 (2016).
Kanagawa et al. "Impaired viability of muscle precursor cells in muscular dystrophy with glycosylation defects and amelioration of its severe phenotype by limited gene expression" Human Molecular Genetics, 22(15):3003-3015 (2013).
Kanagawa et al. "Muscular Dystrophy with Ribitol-Phosphate Deficiency: A Novel Post-Translational Mechanism in Dystroglycanopathy" Journal of Neuromolecular Diseases, 4:259-267 (2017).
Kanagawa et al. "The genetic and molecular basis of muscular dystrophy: roles of cell-matrix linkage in the pathogenesis" J. Hum. Genet., 51:915-926 (2006) (Abstract only).
Kawahara et al. "Zebrafish models for human FKRP muscular dystrophies" Human Molecular Genetics, 19 (4):623-633 (2010).
Keramaris et al. "Expression of glycosylated alpha-dystroglycan in newborn skeletal and cardiac muscles of fukutin related protein (FKRP) mutant mice" Muscle & Nerve, 55(4):582-590 (2017) (Abstract only).
Keramaris-Vrantsis et al. "Fukutin-related protein localizes to the Golgi apparatus and mutations lead to mislocalization in muscle in vivo" Muscle & Nerve, 36(4):455-465 (2007) (Abstract only).
Kuga et al. "Absence of Post-phosphoryl Modification in Dystroglycanopathy Mouse Models and Wild-type Tissues Expressing Non-laminin Binding Form of alpha-Dystroglycan" The Journal of Biological Chemistry, 287(12):9560-9567 (2012).
Kuga et al. "Recent advances in alpha-dystroglycanopathy" Brain Nerve, 63(11):1189-1195 (2011) (Abstract only).
Kunz et al. "Posttranslational modification of alpha-dystroglycan, the cellular receptor for arenaviruses, by the glycosyltransferase LARGE is critical for virus binding" J. Virol., 79:14282-14296 (2005).

Lana et al. "Targeted gene correction of FKRP by CRISPR/Cas9 restores functional glycosylation of alpha-dystroglycan in cortical neurons derived from human induced pluripotent stem cells" bioRxiv, pp. 1-25 (2017).
Lin et al. "Zebrafish Fukutin family proteins link the unfolded protein response with dystroglycanopathies" Human Molecular Genetics, 20(9):1763-1775 (2011).
Lu et al. "Mutations alter secretion of fukutin-related protein" Biochimica et Biophysica Acta, 1802:253-258 (2010).
Manya et al. "Demonstration of mammalian protein O-mannosyltransferase activity: coexpression of POMT1 and POMT2 required for enzymatic activity" Proc. Natl. Acad. Sci. U.S.A., 101:500-505 (2004).
Manya et al. "Glycosylation with ribitol-phosphate in mammals: New insights into the O-mannosyl glycan" Biochimica et Biophysica Acta, 1861(10):2462-2472 (2017) (Abstract only).
Manya et al. "The Muscular Dystrophy Gene TMEM5 Encodes a Ribitol $\beta$1,4-Xylosyltransferase Required for the Functional Glycosylation of Dystroglycan" The Journal of Biological Chemistry, 291(47):24618-24627 (2016).
Manzini et al. "Exome sequencing and functional validation in zebrafish identify GTDC2 mutations as a cause of Walker-Warburg syndrome" Am. J. Hum. Genet., 91:541-547 (2012).
Michele et al. "Post-translational disruption of dystroglycan-ligand interactions in congenital muscular dystrophies" Nature, 418:417-422 (2002) (Abstract only).
Mitchell et al. "Dystroglycan Function is a Novel Determinant of Tumor Growth and Behavior in Prostate Cancer" The Prostate, 73: 398-408 (2013) (Abstract only).
Muntoni et al. "Muscular dystrophies due to glycosylation defects: diagnosis and therapeutic strategies" Current Opinion in Neurology, 24(5):437-442 (2011) (Abstract only).
Nakamura et al. "Drosophila dystroglycan is a target of O-mannosyltransferase activity of two protein O-mannosyltransferases Rotated Abdomen and Twisted" Glycobiology, 20:381-394 (2010).
Poppe et al. "The phenotype of limb-girdle muscular dystrophy type 2I" Neurology, 60:1246-1251 (2003) (Abstract only).
Praissman et al. "The functional O-mannose glycan on alpha-dystroglycan contains a phospho-ribitol primed for matriglycan addition" eLife 5:e14473 (2016).
Qiao et al. "Muscle and Heart Function Restoration in a Limb Girdle Muscular Dystrophy 2I (LGMD2I) Mouse Model by Systemic FKRP Gene Delivery" Mol. Ther., 22:1890-1899 (2014).
Riemersma et al. "Disease mutations in CMP-sialic acid transporter SLC35A1 result in abnormal alpha-dystroglycan O-mannosylation, independent from sialic acid" Human Molecular Genetics, 24(8):2241-2246 (2015).
Riemersma et al. "Human ISPD is a Cytidyltransferase Required for Dystroglycan O-Mannosylation" Chemistry & Biology, 22:1643-1652 (2015).
Roscioli et al. "Mutations in ISPD cause Walker-Warburg syndrome and defective glycosylation of alpha-dystroglycan" Nature Genetics, 44(5):581-585 (2012).
Rosenberg "The Immunotherapy of Solid Cancers Based on Cloning the Genes Encoding Tumor-Rejection Antigens" Annual Review of Medicine, 47:481-491 (1996).
Sheikh et al. "Recent advancements in understanding mammalian O-mannosylation" Glycobiology, 27:806-819 (2017).
Stensland et al. "Prevalence, mutation spectrum and phenotypic variability in Norwegian patients with Limb Girdle Muscular Dystrophy 2I" Neuromuscular Disord.: NMD, 21:41-46 (2011) (Abstract only).
Sugita et al. "A stoichiometric complex of neurexins and dystroglycan in brain" J. Cell Biol., 154:435-445 (2001).
Talts et al. "Binding of the G domains of laminin alpha1 and alpha2 chains and perlecan to heparin, sulfatides, alpha-dystroglycan and several extracellular matrix proteins" EMBO J., 18:863-870 (1999).
Tucker et al. "Overexpression of Mutant FKRP Restores Functional Glycosylation and Improves Dystrophic Phenotype in FKRP Mutant Mice" Mol. Therapy: Nucleic Acids, 11:216-227 (2018).
Tyle, Praveen "Iontophoretic Devices for Drug Delivery" Pharmaceutical Research, 3(6):318-326 (1986).

(56) References Cited

OTHER PUBLICATIONS

Vannoy et al. "Adeno-Associated Virus-Mediated Mini-Agrin Delivery is Unable to Rescue Disease Phenotype in a Mouse Model of Limb Girdle Muscular Dystrophy Type 2I" The American Journal of Pathology, 187(2):431-440 (2017).

Vannoy et al. "Adeno-Associated Virus-Mediated Overexpression of LARGE Rescues a-Dystroglycan Function in Dystrophic Mice with Mutations in the Fukutin-Related Protein" Human Gene Therapy, 25:187-196 (2014).

Vannoy et al. "Efficacy of Gene Therapy is Dependent on Disease Progression in Dystrophic Mice with Mutations in the FKRP Gene" Molecular Therapy: Methods & Clinical Development, 5:31-42 (2017).

Willer et al. "The glucuronyltransferase B4GAT1 is required for initiation of LARGE-mediated alpha-dystroglycan functional glycosylation" eLife 3 24 pages (2014).

Wu et al. "Glucocorticoid Steroid and Alendronate Treatment Alleviates Dystrophic Phenotype with Enhanced Functional Glycosylation of alpha-Dystroglycan in Mouse Model of Limb-Girdle Muscular Dystrophy with FKRPP448L Mutation" Am. J. Pathol., 186:1635-1648 (2016) (Abstract only).

Wu et al. "Long-Term Treatment of Tamoxifen and Raloxifene Alleviates Dystrophic Phenotype and Enhances Muscle Functions of FKRP Dystroglycanopathy" The American Journal of Pathology, 188(4):1069-1080 (2018) (Abstract only).

Xu et al. "Adeno-associated Virus 9 Mediated FKRP Gene Therapy Restores Functional Glycosylation of a-Dystroglycan and Improves Muscle Functions" Molecular Therapy, 21(10):1832-1840 (2013).

Yagi et al. "Direct Mapping of Additional Modifications on Phosphorylated O-glycans of a-Dystroglycan by Mass Spectrometry Analysis in Conjunction with Knocking Out of Causative Genes for Dystroglycanopathy" Molecular & Cellular Proteomics, 15(11):3424-3434 (2016).

Yoshida-Moriguchi "Matriglycan: a novel polysaccharide that links dystroglycan to the basement membrane" Glycobiology, 25:702-713 (2015).

Yoshida-Moriguchi et al. "SGK196 is a glycosylation-specific O-mannose kinase required for dystroglycan function" Science, 341:896-899 (2013).

Yoshioka et al. "Novel FKRP mutations in a Japanese MDC1C sibship clinically diagnosed with Fukuyama congenital muscular dystrophy" Brain & Development, 39(10):869-872 (2017) (Abstract only).

Yu et al. "Adeno-Associated Viral-Mediated Large Gene Therapy Rescues the Muscular Dystrophic Phenotype in Mouse Models of Dystroglycanopathy" Human Gene Therapy, 24:317-330 (2013).

Esser et al. "Loss of LARGE2 Disrupts Functional Glycosylation of alpha-Dystroglycan in Prostate Cancer" The Journal of Biological Chemistry, 288(4):2132-2142 (2013).

\* cited by examiner

COMPOSITIONS AND METHODS FOR TREATING MUSCULAR DYSTROPHY AND OTHER DISORDERS

STATEMENT OF PRIORITY

This application is a divisional of U.S. patent application Ser. No. 15/842,580, filed Dec. 14, 2017 (pending), which claims the benefit, under 35 U.S.C. § 119(e), of U.S. Provisional Application No. 62/435,442, filed Dec. 16, 2016 and U.S. Provisional Application No. 62/520,252, filed Jun. 15, 2017, the entire contents of each of which are incorporated by reference herein.

FIELD OF THE INVENTION

The present invention is directed to pharmaceutical formulations and methods of use thereof in treating muscular dystrophy and other disorders.

BACKGROUND OF THE INVENTION

Dystroglycanopathies are a subset of muscular dystrophies characterized by a secondary defect in glycosylation of alpha-dystroglycan ($\alpha$-DG). The diseases have been linked to autosomal-recessive mutations in at least 18 different genes. They include fukutin-related protein (FKRP), fukutin, like-acetylglucosaminyltransferase (LARGE), POMGnT1, POMT1, POMT2, Isoprenoid Synthase Domain Containing (ISPD), Transmembrane protein 5 (TMEM5), $\beta$1,3-N-acetylglucosaminyltransferase1 (B3GNT1), glycosyltransferase-like domain containing 2 (GTDC2), $\beta$3-N-acetylgalactosaminyltransferase 2 (B3GALNT2), DOLK, GMPPB, DMP2, DMP3 and SGK196. Biochemical studies have established direct evidence for involvement of a number of the genes in glycosylation modifications of $\alpha$-DG. Fukutin and Fukutin related protein (FKRP) genes have been recently proposed as Ribitol-5-P transferase that transfers the phosphorated ribitol to the core sugar chain of $\alpha$-DG. LARGE protein acts as a bifunctional glycosyltransferase, xylosyltransferase and glucuronyltransferase, producing repeating units of [-3-xylose-$\alpha$1,3-glucuronic acid-$\beta$1-] that is the functional glycan chain linking cell membrane protein and extracellular matrix proteins. This LARGE glycan chain is linked to the core O-mannosyl glycans by tandem ribitols. This linkage is critical for muscle health and lack of FKRP function as the result of gene mutations therefore prevents the production of functional glycosylation of $\alpha$-DG, and disrupts normal interaction between membrane and connective tissues, leading to muscle fiber damage and muscular dystrophy.

Mutations in the FKRP gene cause a wide spectrum of disease from a milder form of limb-girdle muscular dystrophy (LGMD2I) to severe Walker-Warburg syndrome (WWS), muscle-eye-brain disease (MEB), and congenital muscular dystrophy type 1D (MDC1D). However, little progress has been made for the treatment of the diseases. There is no effective therapy available and only physical therapy and palliative care are being routinely provided as treatment.

The present invention overcomes previous shortcomings in the art by providing pharmaceutical compositions and methods of their use in treating muscular dystrophy and other disorders.

SUMMARY OF THE INVENTION

In one aspect, the present invention provides a method of enhancing functional glycosylation of alpha-dystroglycan ($\alpha$-DG) in a subject without defects in dystroglycan-related genes and in need thereof, comprising administering to the subject an effective amount of a ribitol, thereby restoring or enhancing functional glycosylation of $\alpha$-DG in the subject.

In a further aspect, the present invention provides a method of treating muscular dystrophy with the levels of ribitol and CDP-ribitol not affected by the diseases, comprising administering to the subject an effective amount of a ribitol, thereby treating the muscular dystrophy in the subject.

An additional aspect of this invention is a method of treating a disorder in a subject associated with a mutation in a fukutin related protein (FKRP) gene, comprising administering to the subject an effective amount of a ribitol, thereby treating the disorder in the subject.

Further provided herein is a method of reducing and/or inhibiting the incidence of a neuronal migration abnormality or other disorder or symptoms associated with a mutation in a FKRP gene in a subject known or suspected to have a mutation in the FKRP gene, comprising administering to the mother of the subject, during the subject's gestation in the mother's uterus, an effective amount of a ribitol, thereby reducing and/or inhibiting the incidence of a neuronal migration abnormality, or other disorder or symptoms associated with a mutation in the FKRP gene of the subject.

In another aspect of this invention, a method is provided of treating or inhibiting the development of muscle weakness in a subject that is a carrier of a mutated FKRP gene, comprising administering to the subject an effective amount of a ribitol, thereby treating muscle weakness, including but not limited to weakness of skeletal muscle, cardiac muscle and respiratory muscle, in the subject.

In another aspect of this invention, a method is provided of treating or inhibiting the development of muscle weakness in a subject that is not related to muscular dystrophy comprising administering to the subject an effective amount of a ribitol, thereby treating muscle weakness, including but not limited to weakness of skeletal muscle, cardiac muscle and respiratory muscle, in the subject.

The present invention is explained in greater detail below.

P448L, and C57 mice. F-α-DG was detected by blotting with IIH6C4 antibody, laminin overlay assay, and AF6868 antibody. Core of α-DG from cardiac tissue (heart) was detected by blotting with AF6868 antibody. Detection of GAPDH was used as loading control. Arrow heads indicate laminin binding bands. The strong bands in laminin binding assay are endogenous laminin present in all samples. (2B) Quantification of IIH6C4 band intensity from western blot. Values were normalized to GAPDH expression for each tissue and presented as % expression compared to C57. Error bars represent mean±SEM. Unpaired t test *p≤0.05.

Figure 3A:
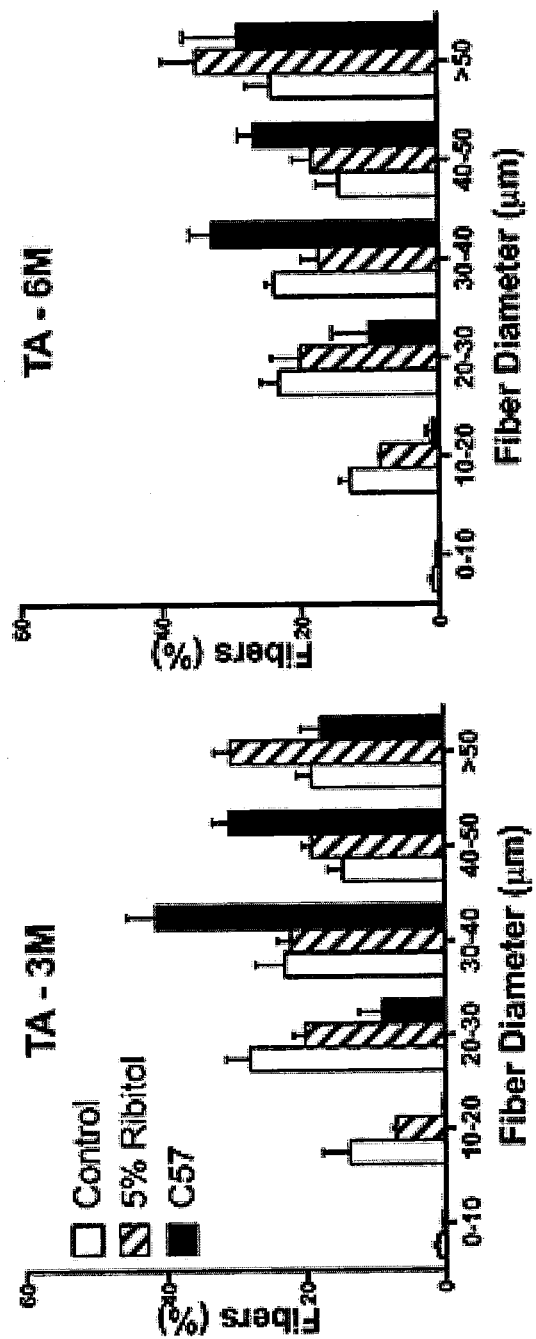
Figure 3B:
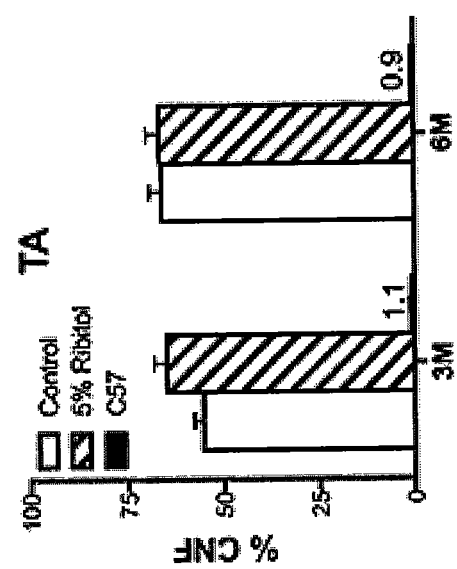

FIGS. 3A-B. Histopathology of muscle tissues from ribitol-treated P448L mice. Seven-week-old P448L mutant mice were given drinking water only (control), or drinking water supplemented with ribitol for either 3 months (3 M) or 6 months (6 M). (3A) Fiber size distribution of TA muscles of either control (n=3) or ribitol treated (n=4) P448L mutant mice, and wild-type C57 mice (n=4). (3B) Percentage of centrally-nucleated fibers in TA muscles of P448L mutant mice treated with ribitol for 3 M and 6 M, or aged matched control P448L mutant mice and wild-type C57 mice. Error bars represent mean±SEM. Unpaired t test *p<0.05.

Figure 4A:
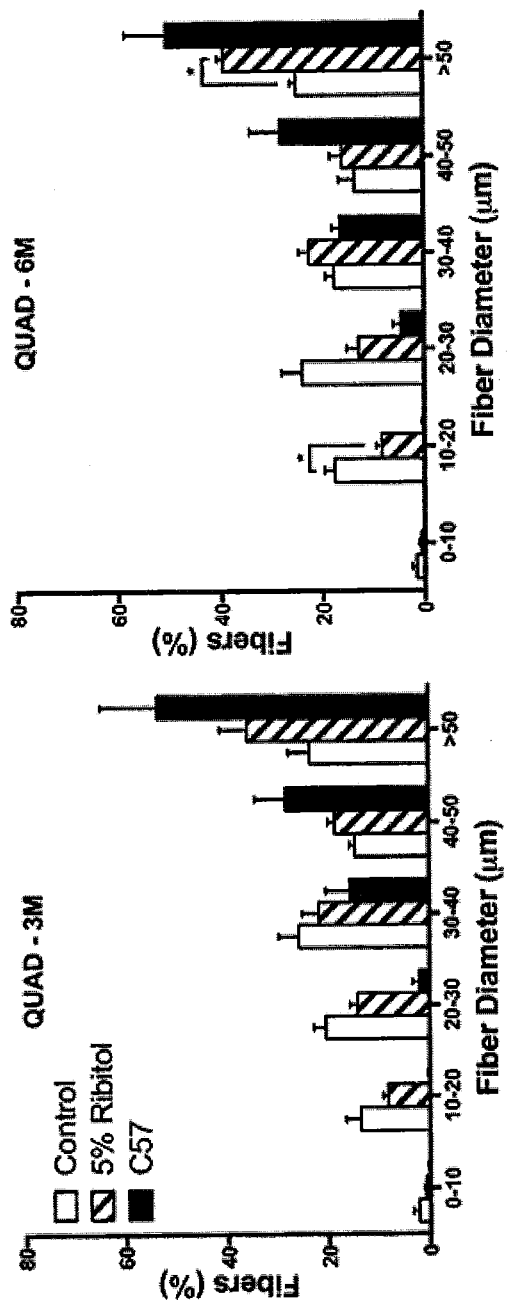
Figure 4B:
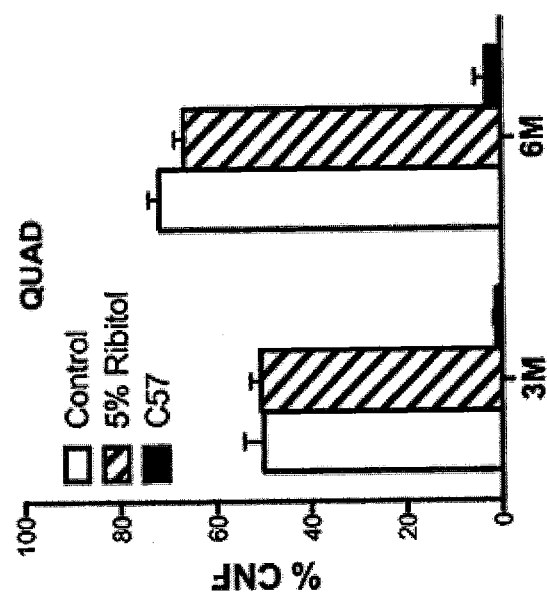

FIGS. 4A-B. Effect of ribitol treatment on histopathology of P448L mutant mice. (4A) Fiber size distribution from quadriceps of either ribitol treated (n=4) or age-matched control (n=3) P448L mutant mice, and wild-type C57 mice (n=4). (4B) Percentage of centrally-nucleated fibers from quadriceps of 3 M and 6 M ribitol treated (n=4) or age-matched control (n=3) P448L mutant mice, and wild-type C57 mice (n=4). Error bars represent mean±SEM. Unpaired t test *p<0.05.

Figure 5:
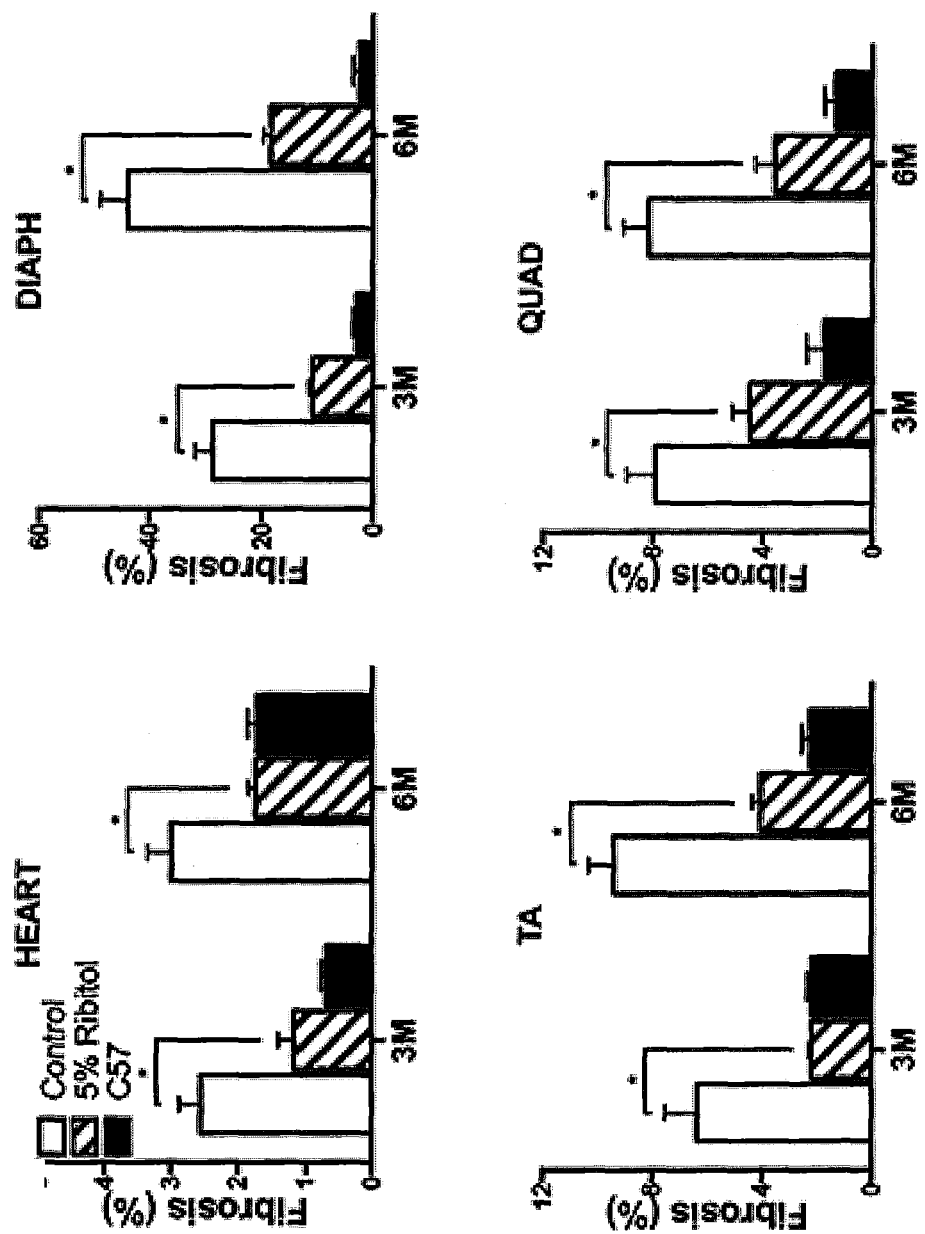

FIG. 5. Effect of ribitol treatment on muscle fibrosis in P448L mutant mice. Seven-week-old P448L mutant mice were given drinking water only (control), or drinking water supplemented with ribitol for either 3 months (3 M) or 6 months (6 M) Percentage of fibrotic areas quantified from Masson's Trichrome staining of heart, diaphragm and TA muscles of either ribitol-treated (for 3 M and 6 M) P448L mutant mice (n=4), or age-matched control P448L mutant mice (n=3) and wild-type C57 mice (n=4). Error bars represent mean±SEM. Unpaired t test *p<0.05.

Figure 6A:
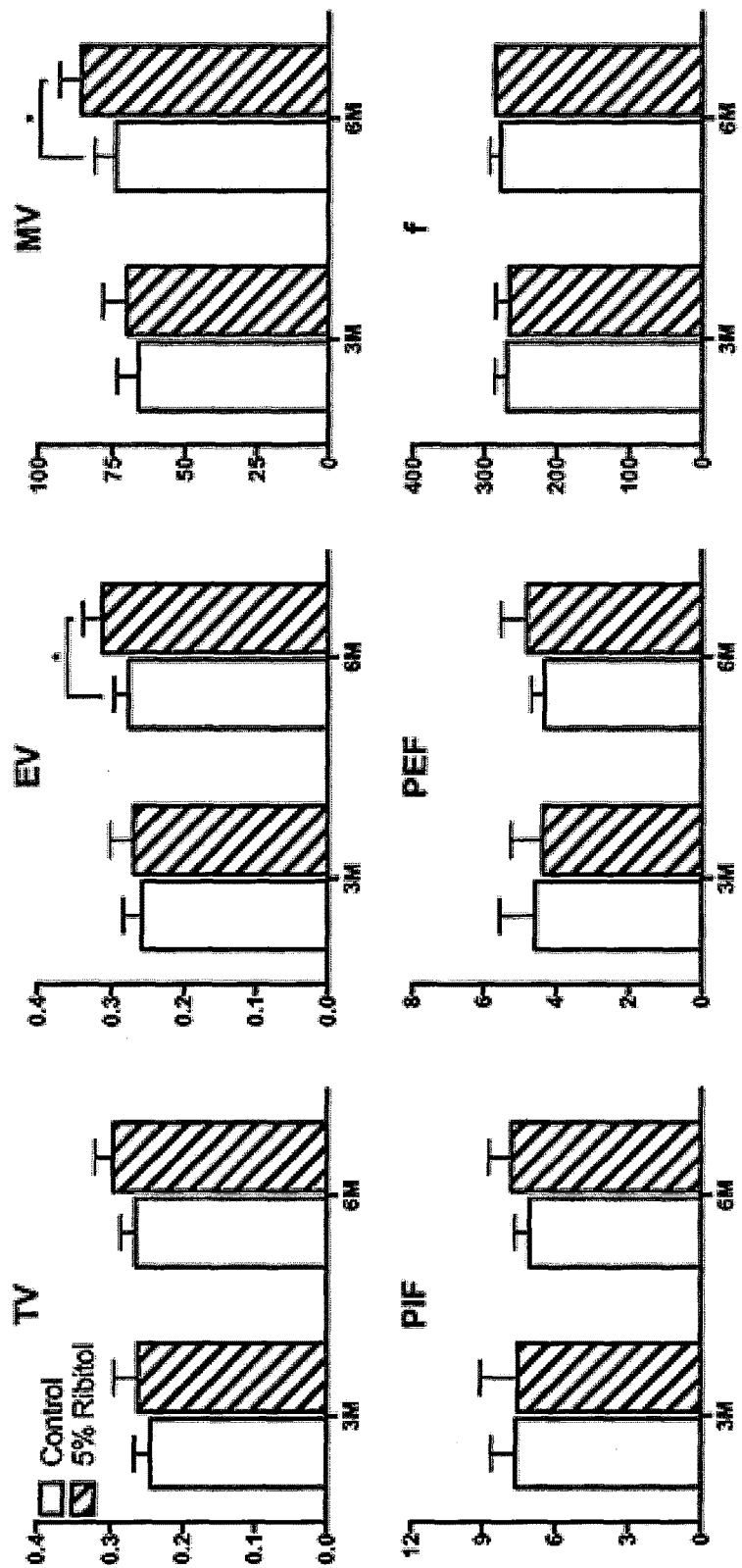
Figure 6B:
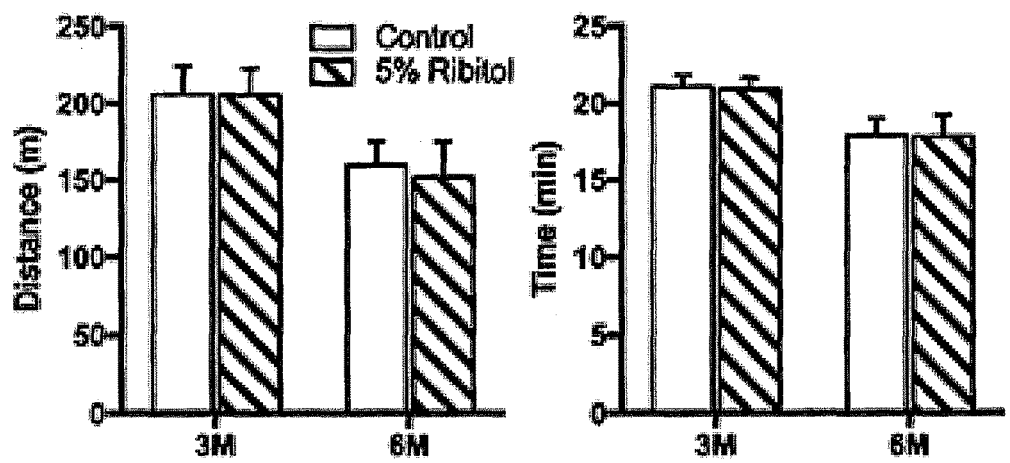
Figure 6C:
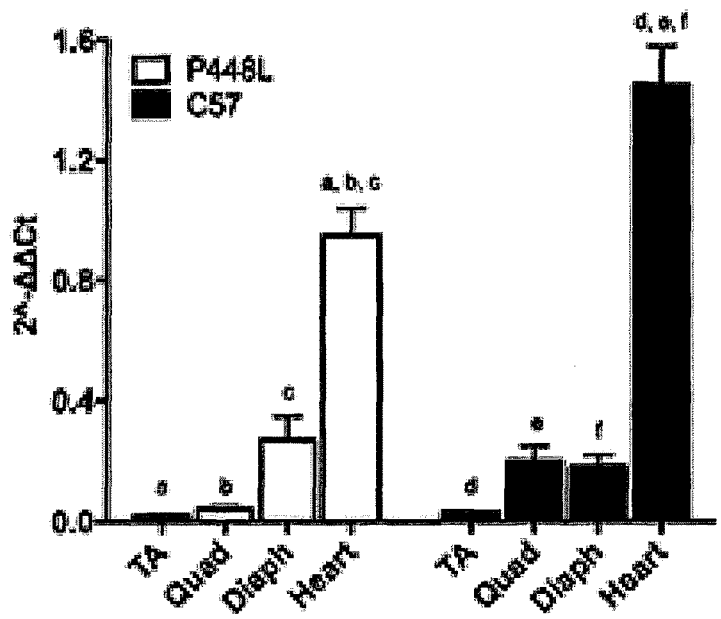

FIGS. 6A-C. Evaluation of muscle and respiratory function on ribitol-treated P448L mutant mouse. Seven-week-old P448L mutant mice were given drinking water only (control), or drinking water supplemented with ribitol for either 3 months (3 M) or 6 months (6 M). (6A) Respiratory function parameters from control or ribitol-treated P448L mice. (TV: tidal volume, EV: expiratory volume, MV: minute volume, PIF: peak inspiratory flow, PEF: peak expiratory flow, and f: breathing frequency). (6B) Treadmill exhaustion test assessing the distance (m) and running time (min) until exhaustion covered by control or ribitol-treated P448L mutant mice. (6C) Levels of FKRP transcript in cardiac and skeletal muscles analyzed by quantitative real-time PCR. Error bars represent mean±SEM. Unpaired t test, *p<0.05. Significance in respiratory function noted with *. Significance in FKRP transcript across tissues noted with same letter.

Figure 7:
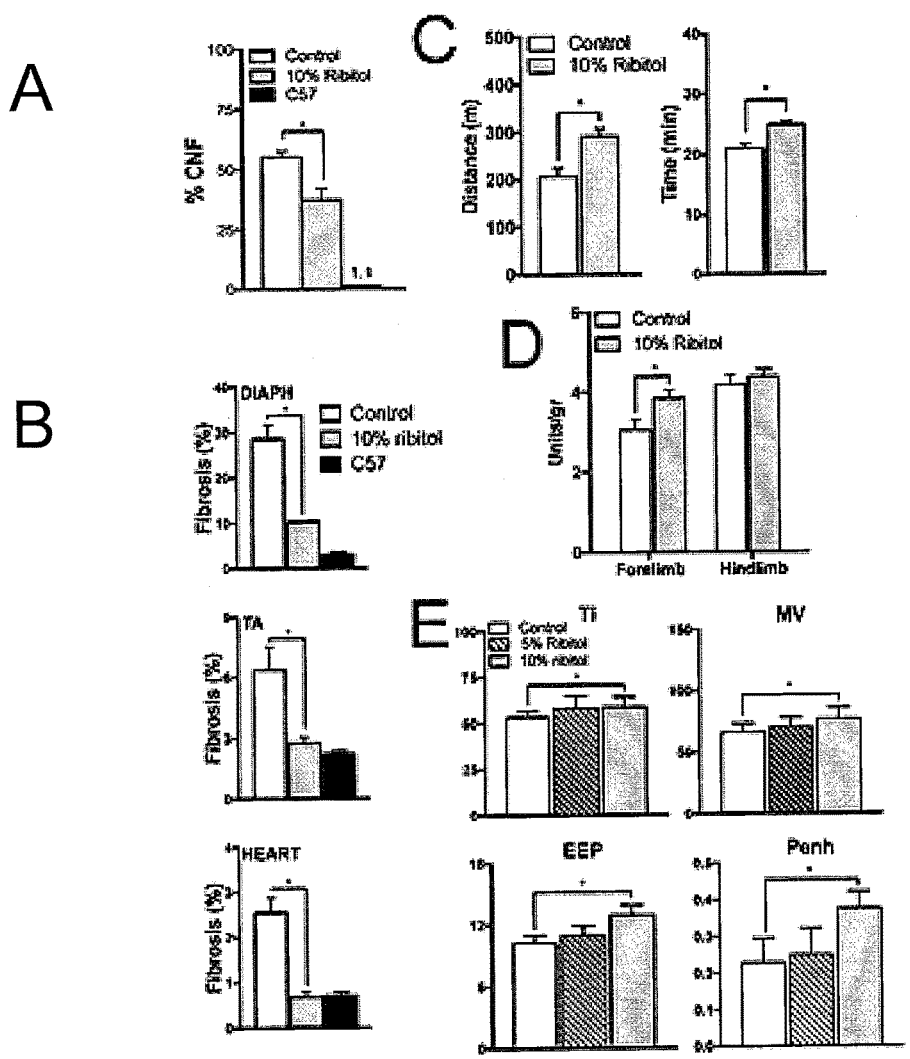

FIG. 7. Effect of early 10% ribitol treatment on histopathology and muscle function of P448L mutant mice. Mice were treated from pregnancy to 19 weeks of age. Control P448L mice were given drinking water only. (Panel A) H&E staining of tibialis anterior (TA) tissues from either control (P448L control), or ribitol-treated (P448L 10% ribitol) mutant mice. Percentage of centrally-nucleated fibers (% CNF) in TA muscles treated with 10% ribitol or aged matched control mutant mice and C57 mice. Scale bar, 50 mm. (Panel B) Masson's Trichrome staining. Percentage of fibrotic areas quantified from the treated, age-matched control P448L mutant mice and C57 mice. (Panel C) Treadmill exhaustion test shows significant improvement in distance (m) and running time (min) for the treated mice in comparison with control (Control). Unpaired t test *p<0.05. (Panel D) Grip strength test in control or 10% ribitol-treated mutant mice at the age of 18 weeks. Force (Unite) is normalized to bodyweight (gr). (Panel E) Respiratory function from control and 10% ribitol-treated P448L mice at 18 weeks of age. (Ti: inspiratory time, MV: minute volume, EEP: expiratory pause, Penh: enhanced pause). Error bars represent mean±SEM. Unpaired t test *p<0.05.

DETAILED DESCRIPTION OF THE INVENTION

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

The disclosures of all patents, patent publications and non-patent documents cited herein are incorporated herein by reference in their entirety.

The present invention is based on the unexpected discovery that ribitol can restore and/or enhance functional glycosylation of mainly alpha-dystroglycan (α-DG) in cells without defects in the genes related to muscular dystrophy and cells with FKRP mutation. Yet, the same functional glycosylated epitope can also modify other proteins. Therefore, restored or enhanced functional glycosylation by ribitol is not limited to α-DG and the use of the phrase "functional glycosylation of α-DG" represents functional glycosylation of any protein after the use of ribitol.

Thus, in one embodiment, the present invention provides a method of restoring and/or enhancing functional glycosylation of alpha-dystroglycan (α-DG) in a subject without defects in dystroglycan-related genes and in need thereof, comprising administering to the subject an effective amount of a ribitol, thereby restoring and/or enhancing functional glycosylation of α-DG in the subject.

The present invention also provides a method of treating muscular dystrophy without defects in dystroglycan-related genes (e.g., a muscular dystrophy that is not associated with a defect in glycosylation of α-DG) or defects or abnormalities in levels of the ribitol and CDP-ribitol in a subject, comprising administering to the subject an effective amount of a ribitol, thereby treating the muscular dystrophy in the subject.

Furthermore the present invention provides a method of treating a disorder associated with (e.g., caused by or resulting from) a mutation in a fukutin related protein (FKRP) gene in a subject, comprising administering to the subject an effective amount of a ribitol, thereby treating the disorder associated with a mutation in a fukutin related protein (FKRP) gene disorder associated with a mutation in a fukutin related protein (FKRP) gene in the subject.

In an additional embodiment, the present invention provides a method of reducing the incidence of a neuronal migration abnormality or other disorder or symptoms associated with a mutation in a FKRP gene or without defect in a dystroglycan-related gene or in glycosylation of α-DG, comprising administering to the mother of the subject, during the subject's gestation in the mother's uterus, an effective amount of a ribitol, thereby reducing the incidence of a neuronal migration abnormality, or other disorder or symptoms associated with a mutation in the FKRP gene of the subject.

Additionally, the present invention provides a method of treating and/or inhibiting the development of muscle weakness in a subject that is a carrier of a mutated FKRP gene and/or without defect in a dystroglycan-related gene and/or without defect in glycosylation of α-DG, comprising administering to the subject an effective amount of a ribitol, thereby treating muscle weakness. The muscle weakness can include but not limited to weakness of skeletal muscle, cardiac muscle and/or respiratory muscle, in any combination, in the subject.

The methods of this invention can also be used to treat non-muscular dystrophy diseases for which restoration of and/or enhance glycosylation of α-DG would be beneficial and/or therapeutic. A nonlimiting example of such a disease or disorder is a cancer that lacks, or expresses reduced levels of, glycosylated α-DG. The use of ribitol can restore and/or enhance levels of glycosylated α-DG or enhance glycosylation of other cell membrane proteins, thus inhibiting cancer cell growth and metastasis. Many cancer types, including breast cancer, prostate cancer, colon, head and neck cancers show reduced expression of glycosylation of α-DG. Thus, in some embodiments, the present invention provides a method of treating cancer in a subject (e.g., a subject in need thereof), comprising administering to the subject an effective amount of a ribitol, thereby treating the cancer in the subject. The present invention also provides a method of inhibiting and/or reducing metastasis of cancer cells in a subject (e.g., a subject in need thereof), comprising administering to the subject an effective amount of a ribitol, thereby inhibiting and/or reducing metastasis of the cancer cells in the subject.

Nonlimiting examples of a cancer that can be treated according to the methods of this invention include B cell lymphoma, T cell lymphoma, myeloma, leukemia, hematopoietic neoplasias, thymoma, lymphoma, sarcoma, lung cancer, liver cancer, non-Hodgkins lymphoma, Hodgkins lymphoma, uterine cancer, cervical cancer, endometrial cancer, adenocarcinoma, breast cancer, pancreatic cancer, colon cancer, anal cancer, lung cancer, renal cancer, bladder cancer, liver cancer, prostate cancer, ovarian cancer, primary or metastatic melanoma, squamous cell carcinoma, basal cell carcinoma, brain cancer, angiosarcoma, hemangiosarcoma, head and neck carcinoma, thyroid carcinoma, soft tissue sarcoma, bone sarcoma, testicular cancer, gastrointestinal cancer, and any other cancer now known or later identified (see, e.g., Rosenberg (1996) *Ann. Rev. Med.* 47:481-491, the entire contents of which are incorporated by reference herein).

In some embodiments of the methods of this invention, nonlimiting examples of a disorder associated with a mutation in, or loss of function of, the FKRP gene include limb-girdle muscular dystrophy (LGMD2I), Walker-Warburg syndrome (WWS), muscle-eye-brain disease (MEB), congenital muscular dystrophy type 1C (MDC1C), any other disorder associated with a mutation in, or loss of function of, the FKRP gene, and any combination thereof.

In the methods of this invention, the ribitol can be, but is not limited to, ribitol (adonitol) pentose alcohol, with or without modifications such as tri-acetylated ribitol (Ribitol (OAc)$_3$, per-acetylated ribitol (Ribitol(OAc)$_5$, a precursor thereof, such as ribose, a polysaccharide thereof, a phosphate form thereof, a non-phosphated form thereof, any precursor of a phosphate form, such as Ribose-5-P, any nucleotide form of ribitol (e.g., a nucleotide-alditol having cytosine or other bases as the nucleobase with 1, 2 or 3 phosphate groups and ribitol as the alditol portion), such as CDP-ribitol, CDP-ribitol-OAc2 and any combination or derivative or modification thereof.

The active compound of this invention (e.g., ribitol) can be present in a pharmaceutical formulation that comprises substances and/or agents that are not natural products. As a nonlimiting example, the active compound (e.g., ribitol) of this invention can be present in a pharmaceutical composition with polyethylene glycol (PEG), which in some embodiments can have a molecular weight (MW) in a range of about 200 to about 500. In some embodiments, a pharmaceutical composition of this invention can comprise glucose.

In some embodiments, the active compound of this invention (e.g., ribitol) can comprise a polyalkylene glycol moiety coupled or linked thereto. "Polyalkylene glycol" means straight or branched polyalkylene glycol polymers including, but not limited to, polyethylene glycol (PEG), polypropylene glycol (PPG), and polybutylene glycol (PBG), as well as co-polymers of PEG, PPG and PBG in any combination, and includes the monoalkylether of the polyalkylene glycol. Thus, in various embodiments of this invention, the polyalkylene glycol in the compositions of this invention can be, but is not limited to, polyethylene glycol, polypropylene glycol, polybutylene glycol, and any combination thereof.

In certain embodiments, the polyalkylene glycol of the composition is polyethylene glycol or "PEG." The term "PEG subunit" refers to a single polyethylene glycol unit, i.e., —(CH$_2$CH$_2$O)—. Thus, the active compound can be "pegylated." In some embodiments, the PEG can have a molecular weight from about 10,000 g/mol to about 30,000 g/mol.

In some embodiments, the polyalkylene glycol (e.g., PEG) can be non-polydispersed, monodispersed, substantially monodispersed, purely monodispersed, or substantially purely monodispersed.

"Monodispersed" is used to describe a mixture of compounds wherein about 100 percent of the compounds in the mixture have the same molecular weight.

"Substantially monodispersed" is used to describe a mixture of compounds wherein at least about 95 percent of the compounds in the mixture have the same molecular weight.

"Purely monodispersed" is used to describe a mixture of compounds wherein about 100 percent of the compounds in the mixture have the same molecular weight and have the same molecular structure. Thus, a purely monodispersed mixture is a monodispersed mixture, but a monodispersed mixture is not necessarily a purely monodispersed mixture.

"Substantially purely monodispersed" is used to describe a mixture of compounds wherein at least about 95 percent of the compounds in the mixture have the same molecular weight and have the same molecular structure. Thus, a substantially purely monodispersed mixture is a substantially monodispersed mixture, but a substantially monodispersed mixture is not necessarily a substantially purely monodispersed mixture.

In some embodiments of the methods of this invention, ribitol can be administered or delivered to a subject in combination with (e.g., simultaneously, before and/or after) CTP and/or any other nucleotide in an amount effective for enhancing the effect of ribitol on glycosylation of α-DG or other proteins. Furthermore, in the methods of this invention, ribitol can administered with any other therapy (simultaneously, before and/or after), such as steroid therapy and/or FKRP gene therapy to enhance or increase the therapeutic effect.

Further aspects of this invention include the use of ribitol and/or a composition of this invention in the preparation of a medicament for carrying out the methods of this invention.

An additional aspect is the use of ribitol and/or a composition of this invention for carrying out the methods of this invention.

The ribitol of this invention can be in a composition comprising a pharmaceutically acceptable carrier. The therapeutically effective amount or dosage of ribitol of this invention will vary depending on the subject's condition and therapeutic need, and will also depend, among other things, upon the effect or result to be achieved, the status of the subject and/or the route and/or mode of delivery. In some embodiments, ribitol or any other form(s) that can be converted to ribitol, or ribitol phosphate, or nucleotide-ribitol can be delivered orally in drinking water containing from about 0.1 to about 100% concentration of the drug as many times as desirable, e.g., from about 1 time to about 100 times a day. The drug can also be taken as pellet about 1 to about 10 times daily. The total amount of the drug for daily use can be from about 0.001 g to about 500 g depending on the nature and formulation of the drug, the ribitol or modified ribitol with enhanced effect, etc. The drug can be mixed or combined with any substance for improved delivery, absorption, etc.

Ribitols form in many plants and especially in the plant, *Adonis vernalis*, also known as spring pheasant's eye, or false hellebore, or yellow pheasant's eye and others. *Adonis vernalis* belongs to the buttercup family Ranunculaceae. Plants containing ribitols can be administered as the drug for treating FKRP-related diseases and subjects with FKRP mutation and other diseases. Such plants can be directly used as a food supplement, and/or ribitol can be extracted from the plants for administration as described herein.

Administration of the compound or composition of this invention may be by any suitable route, including but not limited to intrathecal injection, subcutaneous, cutaneous, oral, intravenous, intraperitoneal, intramuscular injection, intra-arterial, intratumoral or any intratissue injection, nasal, oral, sublingual, via inhalation, in an implant, in a matrix, in a gel, or any combination thereof.

Definitions.

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of dose (e.g., an amount of a fatty acid) and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, In re Herz, 537 F.2d 549, 551-52, 190 USPQ 461, 463 (CCPA 1976) (emphasis in the original); see also MPEP § 2111.03. Thus, the term "consisting essentially of" when used in a claim of this invention is not intended to be interpreted to be equivalent to "comprising."

"Subject" as used herein includes any animal in which functional glycosylation of alpha-dystroglycan (α-DG) or other proteins is necessary or desired. In some embodiments, the subject is any animal that can receive a beneficial and/or therapeutic effect from restoration of functional glycosylation of alpha-dystroglycan (α-DG) and/or enhancement of glycosylation of α-DG. In some embodiments, the subject is a mammal and in particular embodiments, the subject is a human of any age, race, gender, or ethnicity, etc.

By the term "treat," "treating" or "treatment of" (and grammatical variations thereof) it is meant that the severity of the subject's condition is reduced, at least partially improved or ameliorated and/or that some alleviation, mitigation or decrease in at least one clinical symptom is achieved and/or there is a delay or inhibition in the progression of the disease or disorder.

"Treat," "treating" or "treatment" as used herein also refers to any type of action or administration that imparts a benefit to a subject that has a disease or disorder, including improvement in the condition of the patient (e.g., reduction or amelioration of one or more symptoms), healing, etc.

The terms "therapeutically effective amount," "treatment effective amount" and "effective amount" as used herein are synonymous unless otherwise indicated, and mean an amount of a compound, peptide or composition of the present invention that is sufficient to improve the condition, disease, or disorder being treated and/or achieved the desired benefit or goal (e.g., control of body weight). Those skilled in the art will appreciate that the therapeutic effects need not be complete or curative, as long as some benefit is provided to the subject.

Determination of a therapeutically effective amount, as well as other factors related to effective administration of a compound of the present invention to a subject of this invention, including dosage forms, routes of administration, and frequency of dosing, may depend upon the particulars of the condition that is encountered, including the subject and condition being treated or addressed, the severity of the condition in a particular subject, the particular compound being employed, the particular route of administration being employed, the frequency of dosing, and the particular formulation being employed. Determination of a therapeutically effective treatment regimen for a subject of this invention is within the level of ordinary skill in the medical or veterinarian arts. In clinical use, an effective amount may be the amount that is recommended by the U.S. Food and Drug Administration, or an equivalent foreign agency. The amount of active ingredient that can be combined with the carrier materials to produce a single dosage form varies depending upon the subject being treated and the particular mode of administration.

As used herein, "modulate," "modulates" or "modulation" refers to enhancement (e.g., an increase) or inhibition (e.g., diminished, reduced or suppressed) of the specified activity.

The term "enhancement," "enhance," "enhances," or "enhancing" refers to an increase in the specified parameter (e.g., at least about a 1.1-fold, 1.25-fold, 1.5-fold, 2-fold, 3-fold, 4-fold, 5-fold, 6-fold, 8-fold, 10-fold, twelve-fold, or even fifteen-fold or more increase) and/or an increase in the specified activity of at least about 5%, 10%, 25%, 35%, 40%, 50%, 60%, 75%, 80%, 90%, 95%, 97%, 98%, 99% or 100%.

The term "inhibit," "diminish," "reduce" or "suppress" refers to a decrease in the specified parameter (e.g., at least about a 1.1-fold, 1.25-fold, 1.5-fold, 2-fold, 3-fold, 4-fold, 5-fold, 6-fold, 8-fold, 10-fold, twelve-fold, or even fifteen-fold or more increase) and/or a decrease or reduction in the specified activity of at least about 5%, 10%, 25%, 35%, 40%, 50%, 60%, 75%, 80%, 90%, 95%, 97%, 98%, 99% or 100%. These terms are intended to be relative to a reference or control.

The above terms are relative to a reference or control. For example, in a method of enhancing glycosylation of α-DG in a subject of this invention by administering ribitol to the subject, the enhancement is relative to the amount of glycosylation in a subject (e.g., a control subject) in the absence of administration of ribitol.

"Isolated" as used herein means the ribitol of this invention is sufficiently free of contaminants or cell components with which ribitols may occur. "Isolated" does not mean that the preparation is technically pure (homogeneous), but it is sufficiently pure to provide the ribitol in a form in which it can be used therapeutically.

The term "prevent," "preventing" or "prevention of" (and grammatical variations thereof) refers to prevention and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression is less than what would occur in the absence of the present invention.

A "prevention effective" amount as used herein is an amount that is sufficient to prevent (as defined herein) the disease, disorder and/or clinical symptom in the subject. Those skilled in the art will appreciate that the level of prevention need not be complete, as long as some benefit is provided to the subject.

"Concurrently administering" or "concurrently administer" as used herein means that the two or more compounds or compositions are administered closely enough in time to produce a combined effect (that is, concurrently may be simultaneously, or it may be two or more events occurring within a short time period before and/or after each other, e.g., sequentially). Simultaneous concurrent administration may be carried out by mixing the compounds prior to administration, or by administering the compounds at the same point in time but at different anatomic sites and/or by using different routes of administration.

"Pharmaceutically acceptable" as used herein means that the compound or composition is suitable for administration to a subject to achieve the treatments described herein, without unduly deleterious side effects in light of the severity of the disease and necessity of the treatment.

Pharmaceutical Formulations.

The active compounds described herein may be formulated for administration in a pharmaceutical carrier in accordance with known techniques. See, e.g., Remington, *The Science and Practice of Pharmacy* (21$^{st}$ Ed. 2005). In the manufacture of a pharmaceutical formulation according to the invention, the active compound is typically admixed with, inter alia, an acceptable carrier. The carrier must, of course, be acceptable in the sense of being compatible with any other ingredients in the formulation and must not be deleterious to the subject. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well-known techniques of pharmacy comprising admixing the components, optionally including one or more accessory ingredients.

Furthermore, a "pharmaceutically acceptable" component such as a sugar, carrier, excipient or diluent of a composition according to the present invention is a component that (i) is compatible with the other ingredients of the composition in that it can be combined with the compositions of the present invention without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable components include any of the standard pharmaceutical carriers such as saline solutions, water, emulsions such as oil/water emulsion, microemulsions and various types of wetting agents.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound(s), which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound(s), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to active compound(s), the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

In some embodiments of this invention, the compound of this invention is present in an aqueous solution for subcutaneous administration. In some embodiments, the compound is provided as a lyophilized powder that is reconstituted and administered subcutaneously.

The present invention is illustrated in the following non-limiting examples.

EXAMPLES

Example 1

Currently, no disease specific treatment for FKRP-related diseases and any of glycosylation deficient muscular dystrophy is available. Glucocorticoid steroids (steroids) have been reported for the alleviation of disease symptoms with limited benefit, and largely based on results from its reported uses in Duchenne muscular dystrophy. Therapeutic potential is believed to be achieved through its anti-inflammatory effects. However, benefits of steroids to any muscular dystrophy often last only a limited time period and are always associated with severe side effects including dramatic weight gain and reduction in bone mineral density, osteoporosis and growth retardation. Physical therapy and palliative care are routinely provided but only serve to relieve symptoms and are unable to delay disease progression. Currently there are several potential therapies including AAV gene therapy and gene correction in preclinical development for dystroglycanopathies, but none of them has enter the stage of clinic trials.

The use of viruses for gene and other expression vector delivery greatly increase their risks of immune response, non-target tissue expression, long-term toxicity of the over-expressed gene product and alteration of genomic sequence. The potential risks delay the progress in clinical trials. Further, their efficacy in clinic remains to be proved.

All available treatments, including use of steroids and physical therapy can only achieve relief of symptoms, such as inflammation and pain, but cannot effectively delay disease progression. Use of steroids is always associated with severe side effects, including dramatic weight gain and reduction in bone mineral density, causing osteoporosis and growth retardation. Both short term and long-term safety of the use of extremely large quantity of virus for systemic delivery which is essential for achieving therapeutic value remain to be investigated and cannot be easily determined.

There is no similar approach of using sugar either as monosaccharides or polysaccharides for treatment of muscular dystrophy. No sugar related therapy for muscular dystrophy has ever been trialed to the inventor's knowledge.

There is no similar approach of sugar either as monosaccharides or polysaccharides for treatment of any cancer of which reduced glycosylation or loss of glycosylation of α-DG is related to tumor progression and metastasis.

This invention identifies the use of a sugar, ribitol (adonitol) pentose alcohol, or any of its precursors, polysaccharides, phosphated or non-phosphated forms, and nucleotide-forms (nucleotide-alditol having cytosine or other bases as the nucleobase and ribitol as the alditol portion) for the treatment of subjects with muscular dystrophies and, especially for FKRP-mutation-related muscular dystrophies. This treatment achieves therapeutic effect likely through the restoration of functional glycosylation of α-DG, which is lacking in subjects with FKRP mutations. This restoration reestablishes effective linkage between the muscle cells and the connective tissue surrounding fibers, thus preventing damage to muscles.

Thus, in some embodiments, this invention applies the sugar ribitol as the drug for treatment of muscular dystrophy, including those types caused by mutations in the FKRP gene. Mutations in the FKRP gene cause muscular dystrophy with lack of functional glycosylation of alpha-dystroglycan (α-DG) as the characteristic biochemical marker in the diseased tissues. Mouse models with the same FKRP mutations present the same biochemical feature as patients' tissues, most prominently muscles (Chan et al. "Fukutin-related protein is essential for mouse muscle, brain and eye development and mutation recapitulates the wide clinical spectrums of dystroglycanopathies" *Hum Mol Genet* 19(20): 3995-4006 (2010); Blaeser et al. "Mouse models of fukutin-related protein mutations show a wide range of disease phenotypes" *Hum Genet* 132(8):923-934 (2013)). Using immunohistochemistry with a specific antibody, IIH6, to the functional glycosylated α-DG, muscle fibers from both skeletal and cardiac muscles of FKRP P448L mutant mice produce a significantly decreased amount to almost completely no functional glycosylated α-DG. This can also be demonstrated by western blot detection. Histologically, the diseased muscles undergo continuous degeneration indicated by the presence of degenerating muscle fibers, variation in fiber size, presence of centrally nucleated fibers (a result of regeneration as a consequence of muscle damage) and inflammatory cells and increase in non-fiber connective tissues. Surprisingly, feeding FKRP-P448L mutant dystrophic mice with ribitols either in drinking water or gavage, significantly increased the levels of functionally glycosylated α-DG in skeletal muscles demonstrated by immunohistochemistry. More surprising, the level of F-α-DG is even stronger in the cardiac muscle than in the skeletal muscles, reaching signal intensity to levels similar to that detected in normal muscles. This is consistent in all mice treated with ribitols.

It is generally understood that IIH6 antibody detects functional glycosylated α-DG, which representing the functional form of sugar modification. However, the epitope detected by the IIH6 antibody may not be limited to the α-DG. Further, other forms of functionally glycosylated epitopes are likely present on α-DG and other proteins, and can be enhanced by ribitol.

Ribitol treatment for 1.5 months improved muscle pathology with a reduction in the number of centrally nucleated fibers (CNF) and inflammation. This can be most clearly demonstrated in the diseased diaphragm, which undergoes more severe and progressive degeneration and fibrosis.

The use of ribitol sugar as a drug provides the ideal means to treat these diseases. No toxicity other than the effect of sugars is expected. This novel therapy not only can be universally applied to all patients with FKRP mutations, it can also be applied to women who are pregnant with a possible disease-carrying child. Carriers of an FKRP mutation, e.g., with a certain degree of muscle weakness, could benefit from the enhanced glycosylation of α-DG resulting from treatment with ribitol.

The drug can be administered to subjects with a single copy of FKRP mutation (heterozygotes, one copy of the FKRP gene is normal) and without obvious muscular dystrophy or other symptoms. The drug can be delivered in any way described as for a muscular dystrophy patient, preferably with reduced dosage.

The drug can be administered to pregnant individuals with one fourth chance of having a baby that has FKRP-mutation related muscular dystrophy. The drug can be delivered in any way described as for a muscular dystrophy patient.

Figure 1:
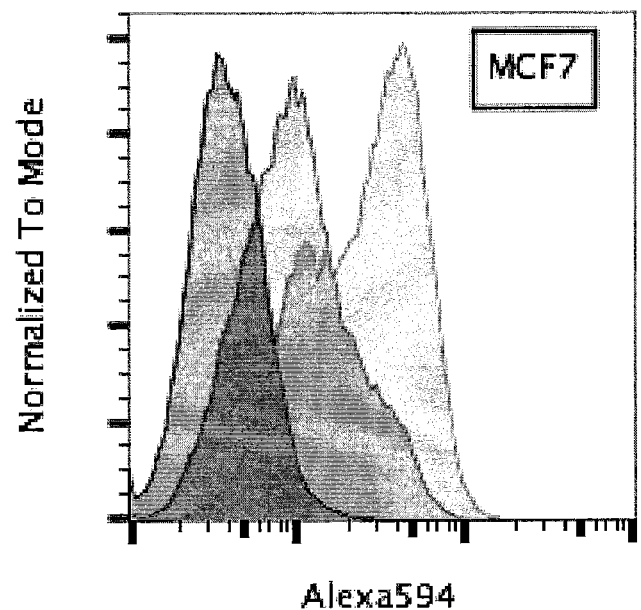
FIG. 1. Fluorescence-activated cell sorting (FACS) for the enhanced expression of glycosylated alpha-DG after ribitol treatment. The breast cancer cell line MCF-7 was seeded in T25 culture flasks and cultured to 75% confluence in DMEM 10% FBS, and then treated with 10 mM ribitol in the same growth medium for 3 days. The cells were then collected by gentle scrapping and washed twice with PBS. The cells were resuspended in 100 microliter PBS and stained with monoclonal antibody IIH6 (Millipore EMD, 1:100 dilution) for 40 minutes and detected with secondary Alexa 594-labeled goat anti-mouse IgM (Invitrogen). The stained cells were washed and then FACS analyzed for the percentage of positive cells and the signal intensity (Alexa594.007). Untreated MCF-7 cells cultured under the same conditions probed with secondary antibody only (Alexa594.005) and with both IIH6 and the secondary antibody (Alexa594.006) are used as controls.

Fluorescence-activated cell sorting (FACS) was used to show enhanced expression of glycosylated alpha-DG after ribitol treatment. The breast cancer cell line MCF-7 was seeded in T25 culture flasks and cultured to 75% confluence in DMEM 10% FBS, and then treated with 10 mM ribitol in the same growth medium for 3 days. The cells were then collected by gentle scrapping and washed twice with PBS. The cells were resuspended in 100 microliter PBS and stained with monoclonal antibody IIH6 (Millipore EMD, 1:100 dilution) for 40 minutes and detected with secondary Alexa 594-labeled goat anti-mouse IgM (Invitrogen). The stained cells were washed and then FACS analyzed for the percentage of positive cells and the signal intensity (Alexa594.007). Untreated MCF-7 cells cultured under the same conditions probed with secondary antibody only (Alexa594.005) and with both IIH6 and the secondary antibody (Alexa594.006) are used as controls. The cells treated with ribitol and detected with the IIH6 antibody showed clearly higher levels of glycosylated alpha-DG with 82% positive cells compared to the untreated controls with only 45% positive cells (FIG. 1).

We first tried the overexpression of ISPD to FKRP P448L mutant mice to see if increasing the activity of the gene can increase the levels of CDP-ribitol and improve the glycosylation status of the α-DG in the FKRP mutant mouse models. However, no clear improvement has so far been observed. It is therefore a great surprise that supplementation with ribitols can improve the glycosylation of α-DG significantly in animals with both copies of the FKRP gene mutated. It is not understood how ribitols can be delivered to diseased muscle effectively as no one has ever reported the use of ribitol for any medical treatment to the inventor's knowledge. It is even more surprising that the effect of ribitol on glycosylation of α-DG is greater in the cardiac muscle than in the skeletal muscle.

Example 2

Mutations in Fukutin Related Protein (FKRP) gene cause dystroglycanopathy characterized by defects in the O-mannosylation of alpha dystroglycan (α-DG). FKRP functions as a ribitol-5-Phosphate (Rbo5P) transferase and is essential for the synthesis of functionally glycosylated α-DG (F-α-DG). We tested the hypothesis that increase in levels of ribitol, a precursor of FKRP substrate, could enhance the transferase efficiency of mutant FKRPs, most of which retain at least partial function. We demonstrate that ribitol supplementation systemically restored therapeutic levels of F-α-DG in both skeletal and cardiac muscles, and importantly improved muscle pathology and function in an FKRP mutant model. Supplementation of ribitol or its derivatives presents a new approach to compensate for the defect in glycosylation of α-DG with potential to treat more than 90% of FKRP dystroglycanopathies.

Mutations in the FKRP gene cause muscular dystrophies with a wide variation in severity from mild limb girdle muscular dystrophy (LGMD) 2I to severe congenital muscular dystrophy (CMD), Walker-Warburg syndrome, and muscle-eye-brain disease. Mild LGMD2I is presented predominantly as myopathy with progressive degeneration involving both skeletal and cardiac muscles. The continuous loss of muscle fibers and diminishing capacity of regeneration eventually lead to the loss of muscle volume and increase in fibrotic tissues. Consequently, patients gradually lose mobility with impaired and ultimately failure of respiratory and cardiac functions. The severe forms of the disease can affect central nerve and optical systems with developmental delay and mental retardation. Currently no treatment is available although several experimental therapies are being tested pre-clinically.

FKRP-related muscular dystrophies belong to a subset of the disease characterized by a common secondary biochemical defect in the glycosylation of alpha-dystroglycan (α-DG). Alpha-DG is a peripheral membrane protein extensively glycosylated with both N- and O-linked glycans, the latter acting as a cellular receptor for laminin and other extracellular matrix (ECM) proteins, including agrin, perlecan, neurexin and pikachurin. Importantly, the interaction of α-DG with ECM proteins is critical for maintaining muscle integrity. The structure of the laminin-binding O-mannosylated glycan on the functionally glycosylated α-DG (F-α-DG) has recently been delineated with the following chain: (3GlcA-1-3Xyl-1)n-3GlcA-1-4Xyl-Rbo5P-1Rbo5P-3GalNAc-1-3GlcNAc-1-4(P-6)Man-1-Thr/ser. The entire process of the glycan chain extension pathway is completed by the following proposed transferase activity, sequentially: POMT1 and POMT2 catalyze the initial O-mannosylation of the proteins. Further extension of the sugar chain is carried out by POMGnT2 (GTDC2) and B3GALNT2, FKTN, FKRP, TMEM5 and B4GAT1 successively. Finally, LARGE acts as a bifunctional glycosyltransferase having both xylosyltransferase and glucuronyltransferase activities, producing repeated units of 3GlcA-1-3Xyl-1.

This study employed FKRP mutant mice containing a P448L mutation which is associated with a severe dystrophic phenotype in clinic. Our results show that ribitol supplementation can effectively restore therapeutic levels of F-α-DG and significantly improve muscle pathology. Partial improvement in muscle functions is also achieved without obvious side effects. This constitutes a potentially effective and safe treatment to the diseases.

One Month Treatment with Ribitol Increases Glycosylation of α-DG in Cardiac and Skeletal Muscles.

In the pilot experiment, 4-week-old P448L mice were treated with drinking water supplemented with 5% ribitol for 1 month. Glycosylation of α-DG was analyzed by immunohistochemistry with a monoclonal antibody, IIH6C4, specifically recognizing the laminin-binding epitopes of F-α-DG. As expected, F-α-DG was undetectable in skeletal muscles of the drinking water only control P448L mice, except for isolated or small clusters of revertant fibers in the diaphragm and tibialis anterior (TA) muscles. The revertant fibers expressed variable levels of F-α-DG as reported previously. Occasionally one or two fibers expressing F-α-DG over the entire cross section area were also observed in cardiac muscle of the control P448L mice. In contrast, oral ribitol supplementation visibly increased the signal of F-α-DG in the heart, diaphragm and limb muscles of the treated mice. Membrane staining with IIH6C4 was observed in the majority of fibers from the limb muscles although most of them were only stained weakly. Areas of fibers with strong signals were also detected. The IIH6C4 signals were consistently and clearly detected in the large proportion of diaphragm muscle fibers of the ribitol treated mice, although a small proportion of fibers lacking detectable membrane staining remained. Interestingly, the signals for F-α-DG were easily distinguished and, particularly, more homogenous in the cardiac muscle than in the skeletal muscles. However, the signals for F-α-DG in all the muscles of ribitol-treated mice were significantly weaker when compared to the same muscle of wild-type C57 mice. We also identified that ribose treatment in the same FKRP mouse model achieves enhancement of F-α-DG.

Prolonged Treatment with Ribitol Maintains Enhanced Expression of Functionally Glycosylated α-DG.

Figure 2A:
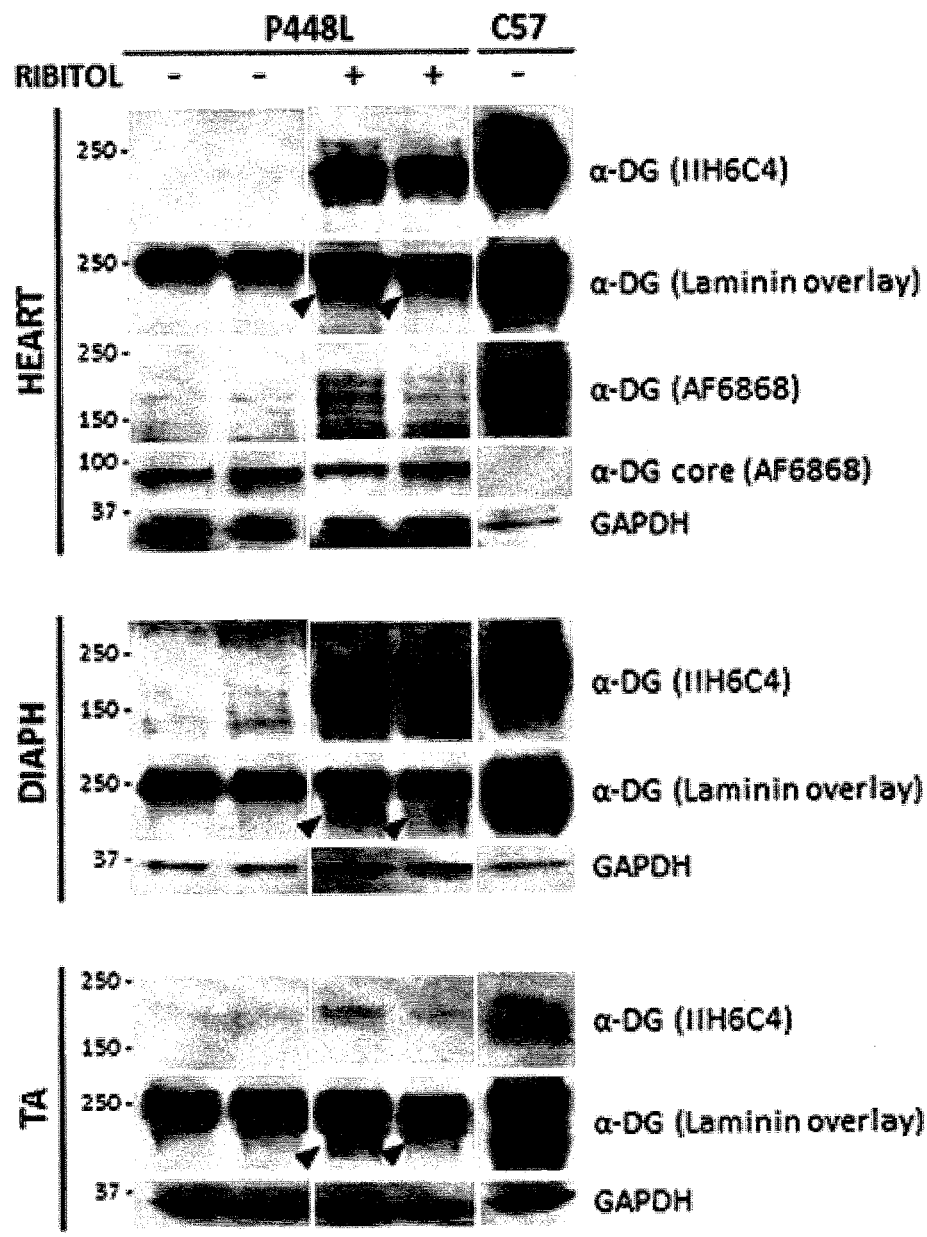
FIGS. 2A-B. Induction of F-$\alpha$-DG in cardiac and skeletal muscles of P448L mice treated with ribitol. Seven-week-old P448L mutant mice were given drinking water only (control), or drinking water supplemented with ribitol for 6 months. (2A) Western blot analysis and laminin overlay assay of protein lysates from heart, diaphragm (diaph), and tibialis anterior (TA) of control (−) or ribitol-treated (+)
Figure 2B:
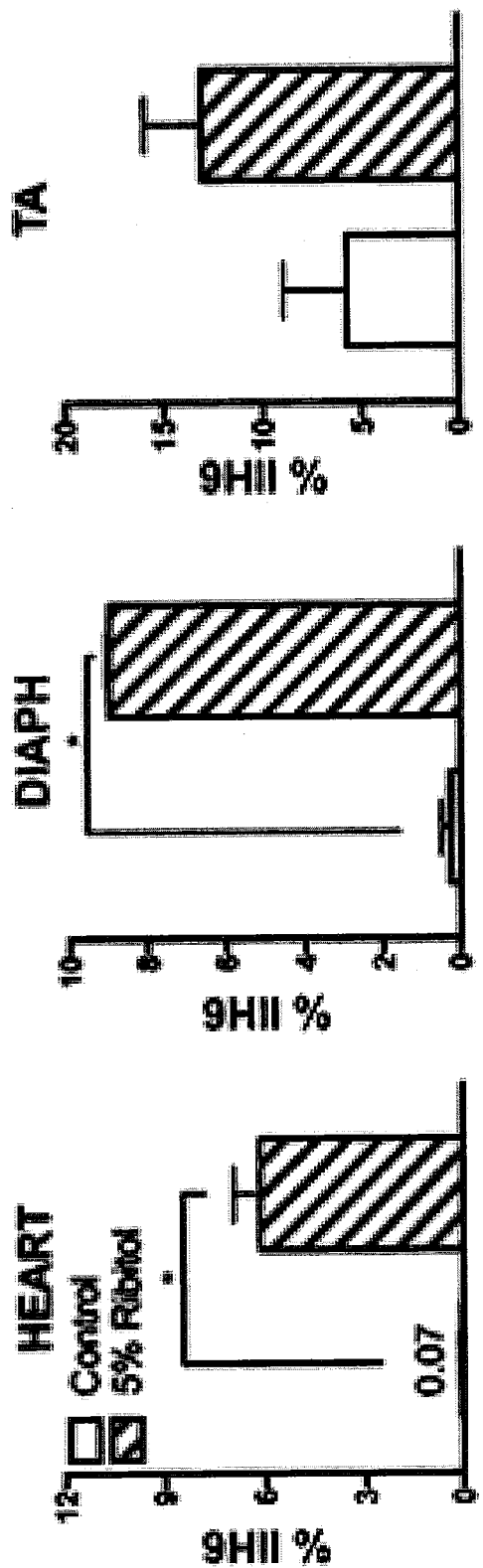

To assess whether ribitol treatment can maintain a long term effect on glycosylation of α-DG and whether such effect could improve disease pathology or slow progression, we extended the treatment of 5% ribitol in drinking water to the P448L mutant mice to 3 and 6 months and examined the expression of F-α-DG of the treated mice in comparison with age-matched P448L controls. Consistent with the 1 month treatment, all of the muscles from the 3 and 6 month treated mice showed a clear increase in the levels of F-α-DG by immunofluorescence staining with the IIH6C4. Tissue distribution of the enhanced F-α-DG remained similar to that in 1 month-treated muscles. Nearly all fibers in the cardiac muscle and the majority of fibers in both diaphragm and limb muscles of treated mice were clearly positive. The signal intensity was homogenous in the cardiac muscle, but varied considerably in the skeletal muscles, especially in the diaphragm where both strong and weak expression were observed within vicinity. The majority of muscle fibers in the TA muscles of treated mice contained weak signals and thus more homogeneous when compared to the signal in the same muscle after 1 month ribitol treatment. Signal distribution and intensity for F-α-DG were generally similar in the same muscles between 3 and 6 month ribitol-treated cohorts. Western blot analysis with the IIH6C4 antibody confirmed the enhanced expression of F-α-DG in the muscles of ribitol-treated P448L mice (FIG. 2A). Consistent with the signal intensity shown by immunofluorescence detection after 6-month treatment, the levels of F-α-DG semi-quantified from the western blot were distinctly detected in the cardiac muscle and diaphragm of ribitol-treated animals, reaching up to 6 and 8% of normal levels in C57 mice, respectively (FIG. 2B). Only trace or indistinguishable signal was detected in the muscles of the control P448L mice. To further confirm the ribitol-induced modification of α-DG, cardiac muscle samples were also analyzed by western blot with the antibody AF6868, which detects both the functionally glycosylated form of α-DG (150-250 kDa as multiple bands) and the core α-DG representing species of non-functionally glycosylated α-DG (core α-DG, 75-100 kDa). Ribitol-treated mice showed detectable, although limited, increase of the higher molecular weight bands representing F-α-DG when compared to the P448L control (FIG. 2A). Similarly, laminin overlay assay demonstrated specific bands of the enhanced F-α-DG in ribitol-treated muscles, although only weakly, supporting the functionality of the ribitol-induced IIH6C4 positive α-DG.

Ribitol Treatment Alleviates Dystrophic Pathology in FKRP P448L Mutant Mice.

To evaluate whether the ribitol-induced increase in levels of F-α-DG is sufficient to improve dystrophic pathology of muscles of the FKRP mutant mice, we performed histology examination of skeletal muscles after 3 and 6 month treatments. H&E staining showed the presence of large areas of degenerating fibers, great variation in fiber sizes and centrally nucleated fibers (CNF) in the skeletal muscles of the control P448L mutant mice. This was also associated with focal inflammatory infiltrates. Treatment with 5% ribitol improved the dystrophic pathology of TA and quadriceps muscles as evidenced by the diminished large foci of necrotic fibers and a more homogenously distributed fiber size. Quantitative analysis from TA and quadriceps showed a considerable decrease in the number of fibers with small-diameters (newly regenerated) indicating a decrease in degeneration after 3 and 6-month ribitol treatment when compared to control mice (FIG. 3A and FIG. 4A, for TA and quadriceps, respectively). However, no difference in percentage of CNF was observed between ribitol treated and control P448L mice (FIG. 3B and FIG. 4B, for TA and quadriceps, respectively). Notably, both 3 and 6 month ribitol treatments significantly decreased areas of fibrotic tissue shown by Masson's Trichrome staining in the TA when compared to control mice. These results together suggest that limited enhancement in F-α-DG nevertheless improves pathology in the diseased limb muscles.

Importantly, ribitol treatment significantly improved pathology of the diaphragm. Large foci of degenerating fibers were common in the control diaphragms but became rarely observed in all mice after 3 and 6 month ribitol treatments, although individual degenerating fibers remained detectable in some of the treated animals. Similarly, focal infiltration was also greatly diminished. The most striking improvement was the degree of fibrosis. The diaphragm of the control mice showed clearly visible fibrosis at the 3 month time point (28.6%), reaching more than 40% after 6 months from initiation of the study, as demonstrated by Masson Trichrome staining. However, the amount of fibrotic tissues in the ribitol-treated cohort was significantly reduced to 11 and 18% after 3 and 6 month treatment, respectively.

The cardiac muscle of the P448L mutant mice has limited pathology with only a small increase in fibrotic area as disease progresses. H&E staining did not show noticeable infiltration and degenerating fibers in both the ribitol treated and the control mice. However, a significant reduction in fibrotic area was observed in the cardiac muscle of both 3 and 6 month ribitol treated groups when compared to the controls (FIG. 5).

Effect of Ribitol Treatment on Respiratory and Skeletal Muscle Functions.

To evaluate the effect of ribitol-induced improvement in F-α-DG on muscle functions, we conducted whole-body plethysmography for respiratory function as well as treadmill exhaustion and grip strength tests for skeletal muscle function at 3-month and 6-month post-initiation of ribitol treatment.

Plethysmography measured respiratory parameters including tidal volume (TV), expiratory volume (EV), minute volume (MV), peak inspiratory flow (PIF), peak expiratory flow (PEF), and breathing frequency (f) (FIG. 6A). The results showed a trend of improvement in TV, EV and MV in both 3 and 6 month ribitol-treated groups compared to the control P448L mutant mice. Improvement was also observed in PIF and PEF at the 6 month time point. Furthermore, improvement in EV and MV reached statistical significance in the 6 month ribitol-treated cohort. However, treadmill and grip force tests did not show a significant difference between ribitol-treated and control P448L mice at both 3 and 6 month time points (FIG. 6B). These results are consistent with a more homogeneous enhancement in expression of F-α-DG and pronounced improvement in pathology in the diaphragm than in the limb skeletal muscles.

During the treatment period, we also weighed mice every 2 weeks until termination. There was no significant change in the percentage of weight gained between ribitol-treated and control P448L mutant mice although body weight of the ribitol-treated female mice was slightly heavier.

Differential Levels of FKRP Expression in Cardiac and Skeletal Muscles.

The differential effect of ribitol treatment on expression of F-α-DG in cardiac and skeletal muscles prompted us to assess whether variation in levels of FKRP expression might be involved. Since no specific antibody is currently available to reliably detect endogenous FKRP protein, quantitative real-time PCR using a mouse FKRP Taqman assay was used to measure the relative levels of FKRP mRNA in different muscles of both wild type C57 and control P448L mutant mice. The heart muscle of both murine models demonstrated the highest expression in FKRP transcripts, significantly (10 times) higher than the skeletal muscles of the same animal model (FIG. 6C). Interestingly, FKRP transcript levels were higher in the diaphragm than those detected in the quadriceps and TA muscles in the P448L mutant mice. This tissue specific variation in FKRP expression levels in both P448L mutant and wild-type models provides an explanation for the differential effect of the ribitol treatment among cardiac and skeletal muscles observed in the FKRP mutant mice.

Effect of Early 10% Ribitol Treatment on Histopathology and Muscle Function of P448L Mutant Mice.

Consistent with the enhancement on the biochemical marker, dystrophic pathology in the 10% ribitol-treated mice was greatly alleviated with significantly fewer CNFs (FIG. 7A). Most fibers of the limb muscles were highly homogenous in shape and size and only a proportion of small CNFs were scattered within the diseased muscles. Notably, improvement in pathology with reduced infiltration and fiber size variation was also observed in the diaphragm. Furthermore, reduction in fibrosis was significant in cardiac muscle, and most prominent in the diaphragm (FIG. 7B).

Importantly, early treatment with 10% ribitol significantly improved skeletal muscle functions of the P448L mice. Treadmill tests showed that both running distance and time of the treated mice were significantly longer than the age-matched control mice (FIG. 7C). Grip strength tests also showed significant improvement on forelimb force from the ribitol-treated mice compared to the control (FIG. 7D). Significant improvement in respiratory functions was also demonstrated by plethysmography (FIG. 7E). Similar to the mutant mice treated for 6 months with 5% ribitol, a trend of improvement in TV, EV and MV was observed, with MV reaching significant difference between the 10% ribitol treated and the control P448L mice. Furthermore, improvement on Ti, EEP and Penh was also significant.

Despite significant advances in understanding the causes and clinical manifestation of the dystroglycanopathies, almost no progress has been made for the treatment of the diseases including those caused by FKRP mutations. Currently, physical therapy and other clinic management routinely provided to patients only serve as palliative care. The only option of pharmacological intervention available is glucocorticoid steroids which are being used anecdotally based on reported benefits from other muscular dystrophies, especially Duchenne muscular dystrophy (DMD). However, clinic efficacy of steroids has not been systematically investigated for dystroglycanopathies and severe side effects including immune suppression and reduction in bone mineral density are reported in dystroglycanopathy mouse model with FKRP mutations. Therefore, there is an urgent need for developing experimental therapies to the diseases. Here we show that ribitol, a natural sugar compound present in some plants and animals and considered as a metabolic intermediate or end-product, can effectively restore therapeutic levels of F-$\alpha$-DG and, more importantly, ameliorate dystroglycanopathy caused by the FKRP P448L mutation which is associated with severe CMD disease phenotype in clinic. Our results demonstrate a potentially safe and effective new treatment for the majority of FKRP dystroglycanopathies and raise the potential of developing similar approaches for other diseases associated with aberrant O-mannosylation of $\alpha$-DG.

Animal Care.

All animal studies were approved by the Institutional Animal Care and Use Committee (IACUC) of Carolinas Medical Center. All mice were housed in the vivarium of Carolinas Medical Center according to animal care guidelines of the institute. Animals were ear tagged prior to group assignment. Food and water were available ad libitum during all phase of the study. Body weight was measured every 2 weeks.

Mouse Model and Experimental Procedure.

FKRP P448L mutant mice were generated by the McColl-Lockwood Laboratory of Muscular Dystrophy Research. These mice contain a homozygous missense mutation (c.1343C>T, p.Pro448Leu) in the FKRP gene with the foxed neomycin resistant (Neo$^r$) cassette removed from the insertion site. C57BL/6 (wild-type/C57) mice were purchased from Jackson Laboratory.

Ribitol was purchased from Sigma (A5502 Adonitol, ≥99%, Sigma, St. Louis) and dissolved in drinking water to the final concentration of 5%. P448L mutant mice aged at 4 weeks were treated with 5% ribitol drinking water for 1 month and P448L mice aged at 7 weeks were treated with 5% ribitol drinking water for 3-months and 6-months with 4-5 mice for each cohort. The levels of drinking solution in the feeding bottles were checked every day. Age-matched P448L mutant and wild-type C57BL/6 mice were used as controls. The animals were terminated at the end of each treatment time point and tissues including heart, diaphragm, TA, quadriceps, liver and kidney were collected for analyses.

Immunohistochemical and Western Blot Analysis.

Tissues were dissected and snap-frozen in dry-ice-chilled-2-methylbutane. For immunohistochemical detection of functionally glycosylated $\alpha$-DG, cross sections of 6 μm thickness were first fixed in ice cold Ethanol:Acetic acid (1:1) for 1 min, blocked with 10% normal goat serum (NGS) in 1× Tris-buffer saline (TBS) for 30 min at room temperature, and incubated overnight at 4° C. with primary mouse monoclonal antibody IIH6C4 (EMD Millipore) (1:500) against $\alpha$-DG. Negative controls received 10% normal goat serum in 1×TBS only. Sections were washed and incubated with secondary AlexaFLuor 488 goat anti-mouse IgM (Invitrogen) (1:500) at room temperature for 1 hr. Sections were washed and finally mounted with fluorescence mounting medium (Dako) containing 1×DAPI (4',6'-diamidino-2-phenylindole) for nuclear staining. Immunofluorescence was visualized using an Olympus BX51/BX52 fluorescence microscope (Opelco) and images were captured using the Olympus DP70 digital camera system (Opelco).

For western blot analysis, tissues were homogenized in extraction buffer (50 mM Tris-HCl pH 8.0, 150 mM NaCl, and 1% Triton X-100), supplemented with 1× protease inhibitor cocktail (Sigma-Aldrich). Protein concentration was quantified by Bradford assay (Bio-Rad DC protein assay). Eighty μg of protein was loaded on an 8-16% Tris-glycine polyacrylamide gel (Life Technologies) and immunoblotted. Nitrocellulose membranes (Bio-Rad) were blocked with 3% milk in 1×PBS for 2 hr at room temperature and then incubated with the following primary antibodies overnight at 4° C.: IIH6C4 (1:2000), AF6868 (R&D Systems) (1:1000), GAPDH (Thermo Fisher) (1:1000). Appropriate horseradish peroxidase (HRP)-conjugated secondary antibodies were incubated for 2 hr at room temperature. All blots were developed by electrochemiluminescence immunodetection (PerkinElmer). For IIH6C4 band quantification from western blot the GelAnalyzer 2010a software was used. For laminin overlay assay, nitrocellulose membranes were blocked with laminin overlay buffer (10 mM ethanolamine, 140 mM NaCl, 1 mM MgCl2, and 1 mM CaCl$_2$, pH 7.4) containing 5% nonfat dry milk for 1 hr at 4° C. followed by incubation with laminin from Engelbreth-Holm-Swarm murine sarcoma basement membrane (L2020) (Sigma) at a concentration of 2 μg/ml overnight at 4° C. in laminin overlay buffer. Membranes were then incubated with rabbit anti-laminin antibody (Sigma) (1:1500) followed by goat anti-rabbit HRP-conjugated IgG secondary antibody (Santa Cruz Biotechnology) (1:3000).

Quantitative Reverse Transcriptase PCR Assay.

Tissue was extracted from shavings of snap frozen muscles of three mice for each group (C57 and P448L). RNA was extracted using TRIzol (Invitrogen) following the supplied protocol. Final RNA pellet was re-suspended in 20 μl RNAse-nuclease free water. Final RNA concentration was determined using Nanodrop 2000c. One μg of RNA was subsequently converted to cDNA using the High-Capacity RNA-to-cDNA™ Kit (Applied Biosystems) following the supplied protocol. cDNA was then used for quantitative real-time PCR using the mouse FKRP-FAM Taqman assay (Mm00557870_m1) with primer limited GAPDH-VIC (Mm99999915_g1) as the internal control and TAQMAN® Universal Master Mix II, with UNG (Life Technologies). Quantitative real time PCR was run on the BioRad CFX96 TOUCH™ Real-Time PCR Detection System (BioRad) following the standard real time PCR conditions suggested for taqman assays. Results of FKRP transcript were calculated and expressed as 2^-$\Delta\Delta$Ct and compared across tissues and animals.

Histopathological and Morphometric Analysis.

Frozen tissues were processed for hematoxylin and eosin (H&E) and Masson's Trichrome staining following standard procedures. Muscle cross-sectional fibers of equivalent diameter were determined from tibialis anterior and quadriceps stained with H&E using MetaMorph v7.7 Software (Molecular Devices). Percentage of centrally nucleated myofibers was manually quantified from the same tissue sections stained with H&E. Fibrotic area represented by blue staining in the Masson's trichrome stained sections was quantified from heart, diaphragm, tibialis anterior and quadriceps using ImageJ software. For all the morphometric analyses, a total of 300 to 400 fibers from two representative 20× magnification images per each muscle per animal were used.

Muscle Function Tests.

For treadmill exhaustion test, mice were placed on the belt of a five-lane-motorized treadmill (Columbus Instruments) supplied with shock grids mounted at the back of the treadmill, which delivered a 0.2-mA current to provide motivation for exercise. Initially, the mice were subjected to an acclimation period (time, 5 min; speed, 8 cm/s, and 0° incline). Immediately after acclimation period, the test commenced with speed increases of 2 cm/s every minute until exhaustion. The test was stopped and the time to exhaustion was determined when the mouse remained on the shock grid for 5 s without attempting to re-engage the treadmill.

For grip force test, forelimb and hind limb in peak torque (g) was measured by a grip strength meter (Columbus Instruments). For forelimb force, the animal was held so that only the forelimb paws grasp the specially designed mouse flat mesh assembly and the mouse pulled back until their grip is broken. The force transducer retains the peak force reached when the animal's grip is broken and is recorded from a digital display. For hind limb force, an angled mesh assembly was used. Mice were allowed to rest on the angled mesh assembly, facing away from the meter with its hind limbs at least one-half of the way down the length of the mesh. The mouse tail was pulled directly toward the meter and parallel to the mesh assembly. During this procedure, the mice resist by grasping the mesh with all four limbs. Pulling toward the meter was continued until the hind limbs released from the mesh assembly. Five successful hind limb and forelimb force measurements within 2 minutes were recorded. The average value was used for analysis. Forelimb and hind limb force are presented as values of KGF (kilogram-force) units normalized to bodyweights (gr) as "Units/gr". All muscle function tests were performed 2 weeks before euthanasia.

Whole Body Plethysmography.

Respiratory functional analysis in conscious, freely moving mice was measured using a whole body plethysmography technique. The plethysmograph apparatus (emka Technologies, Falls Church, Va.) was connected to a ventilation pump for the purpose of maintaining a constant air flow, a differential pressure transducer, a usbAMP signal amplifier, and a computer running EMKA iox2 software with the respiratory flow analyzer module, which was used to detect pressure changes due to breathing and recording the transducer signal. An initial amount of 20 mL of air was injected and withdrawn via a 20 mL syringe into the chamber for the purpose of calibration. Mice were placed inside the "free moving" plethysmograph chamber and allowed to acclimate for 5 min in order to minimize any effects of stress related changes in ventilation. Resting ventilation was measured for a duration of 15 min after the acclimation period. Body temperatures of all mice were assumed to be 37° C. and to remain constant during the ventilation protocol.

Statistical Analysis.

All data are expressed as mean±SEM unless stated otherwise. Statistical analyses were performed with GraphPad Prism version 7.01 for Windows (GraphPad Software). Individual means were compared using multiple t tests. Differences were considered to be statistically significant at $p \leq 0.05$ (*).

Although the present invention has been described with reference to specific details of certain embodiments thereof, it is not intended that such details should be regarded as limitations upon the scope of the invention except as and to the extent that they are included in the accompanying claims.

Throughout this application, various patents and non-patent publications are referenced. The disclosures of these patents and publications in their entireties are hereby incorporated by reference into this application in order to more fully describe the state of the art to which this invention pertains.

That which is claimed is:

1. A method of treating a disorder associated with a mutation or loss of function in a fukutin related protein (FKRP) gene in a subject, comprising administering a therapeutically effective amount of a CDP-ribitol to a subject in need thereof daily for at least 30 days, thereby treating the disorder associated with a mutation or loss of function in a fukutin related protein (FKRP) gene in the subject, wherein the disorder associated with a mutation or loss of function in the FKRP gene is selected from the group consisting of limb-girdle muscular dystrophy (LGMD2I), Walker-Warburg syndrome (WWS), muscle-eye-brain disease (MEB), congenital muscular dystrophy (CMD), and any combination thereof.

2. The method of claim 1, wherein administration of the therapeutically effective amount of the CDP-ribitol treats or reduces the development of muscle weakness.

* * * * *